(12) United States Patent
Goel

(10) Patent No.: US 9,114,249 B2
(45) Date of Patent: Aug. 25, 2015

(54) ASSEMBLY FOR PAIN SUPPRESSING ELECTRICAL STIMULATION OF A PATIENT'S NERVE

(71) Applicant: Amitabh Goel, Wichita, KS (US)

(72) Inventor: Amitabh Goel, Wichita, KS (US)

( * ) Notice: Subject to any disclaimer, the term of this patent is extended or adjusted under 35 U.S.C. 154(b) by 111 days.

(21) Appl. No.: 14/137,354

(22) Filed: Dec. 20, 2013

(65) Prior Publication Data

US 2015/0174395 A1 Jun. 25, 2015

(51) Int. Cl.
*A61N 1/00* (2006.01)
*A61N 1/05* (2006.01)

(52) U.S. Cl.
CPC .................................... *A61N 1/0553* (2013.01)

(58) Field of Classification Search
CPC .. A61N 1/0551; A61N 1/0553; A61N 1/3605
USPC ......................................................... 607/117
See application file for complete search history.

(56) References Cited

U.S. PATENT DOCUMENTS

| | | | |
|---|---|---|---|
| 3,724,467 A | 4/1973 | Avery et al. |
| 3,738,368 A | 6/1973 | Avery et al. |
| 5,360,441 A | 11/1994 | Otten |
| 6,091,979 A | 7/2000 | Madsen |
| 6,161,047 A | 12/2000 | King |
| 6,175,769 B1 | 1/2001 | Errico et al. |
| 6,205,361 B1 | 3/2001 | Kuzma |
| 6,292,702 B1 | 9/2001 | King |
| 6,415,187 B1 | 7/2002 | Kuzma |
| 6,442,435 B2 | 8/2002 | King |
| 6,470,218 B1 | 10/2002 | Behl |
| 6,714,822 B2 | 3/2004 | King et al. |
| 6,745,079 B2 | 6/2004 | King |
| 6,788,966 B2 | 9/2004 | Kenan et al. |
| 6,999,820 B2 | 2/2006 | Jordan |
| 7,191,018 B2 | 3/2007 | Gielen et al. |
| 7,231,259 B2 | 6/2007 | Jenney et al. |
| 7,308,318 B2 | 12/2007 | Miazga et al. |
| 7,376,468 B2 | 5/2008 | King et al. |
| 7,613,524 B2 | 11/2009 | Jordan |
| 7,617,006 B2 | 11/2009 | Metzler et al. |
| 2001/0023367 A1 | 9/2001 | King et al. |

(Continued)

OTHER PUBLICATIONS

Author: Unknown; Medtronic, 1 × 4 74001 2 × 4 74002 Pocket adaptor kit for spinal stimulation; Implant manual; Jul. 2009; vol./Issue # N/A; Publisher: Medtronic, Inc.; Publication location: Minneapolis, Minnesota, US; p. 5.

*Primary Examiner* — Christopher D Koharski
*Assistant Examiner* — Philip Edwards
(74) *Attorney, Agent, or Firm* — Kenneth H. Jack; Davis & Jack, L.L.C.

(57) ABSTRACT

An assembly for pain suppressing electrical stimulation of a patient's nerve, the assembly including lateral, medial, and oppositely lateral series of contact plates; a lateral panel, a medial panel and an oppositely lateral panel, the electrical contact plates being fixedly attached to the panels; living hinges pivotally attaching the lateral and oppositely lateral panels to the medial panel; proximally extending wires electrically communicating with the contact plates; a proximally extending insulator attached to the medial panel, the insulator having a hollow bore and the wires being embedded within the insulator; a proximally opening traction socket fixedly attached to the medial panel; and a semi-rigid stay which is extendable through the hollow bore, the semi-rigid stay being engageable with the proximally opening traction socket.

6 Claims, 6 Drawing Sheets

(56) References Cited

U.S. PATENT DOCUMENTS

| | | |
|---|---|---|
| 2002/0151948 A1 | 10/2002 | King et al. |
| 2004/0186543 A1 | 9/2004 | King et al. |
| 2004/0243208 A1 | 12/2004 | Jordan |
| 2005/0203600 A1 | 9/2005 | Wallace |
| 2006/0161236 A1 | 7/2006 | King |
| 2006/0178718 A1 | 8/2006 | Jordan |
| 2006/0259110 A1 | 11/2006 | Wallace et al. |
| 2007/0027514 A1 | 2/2007 | Gerber |
| 2007/0055332 A1 | 3/2007 | Swoyer |
| 2007/0060991 A1 | 3/2007 | North et al. |
| 2007/0142889 A1 | 6/2007 | Whitehurst et al. |
| 2007/0179579 A1 | 8/2007 | Feler et al. |
| 2007/0191709 A1 | 8/2007 | Swanson |
| 2007/0255372 A1 | 11/2007 | Metzler et al. |
| 2007/0255373 A1 | 11/2007 | Metzler |
| 2007/0265691 A1 | 11/2007 | Swanson |
| 2008/0103576 A1 | 5/2008 | Gerber |
| 2008/0161670 A1 | 7/2008 | King et al. |
| 2008/0228250 A1 | 9/2008 | Mironer |
| 2009/0270957 A1 | 10/2009 | Pianca et al. |

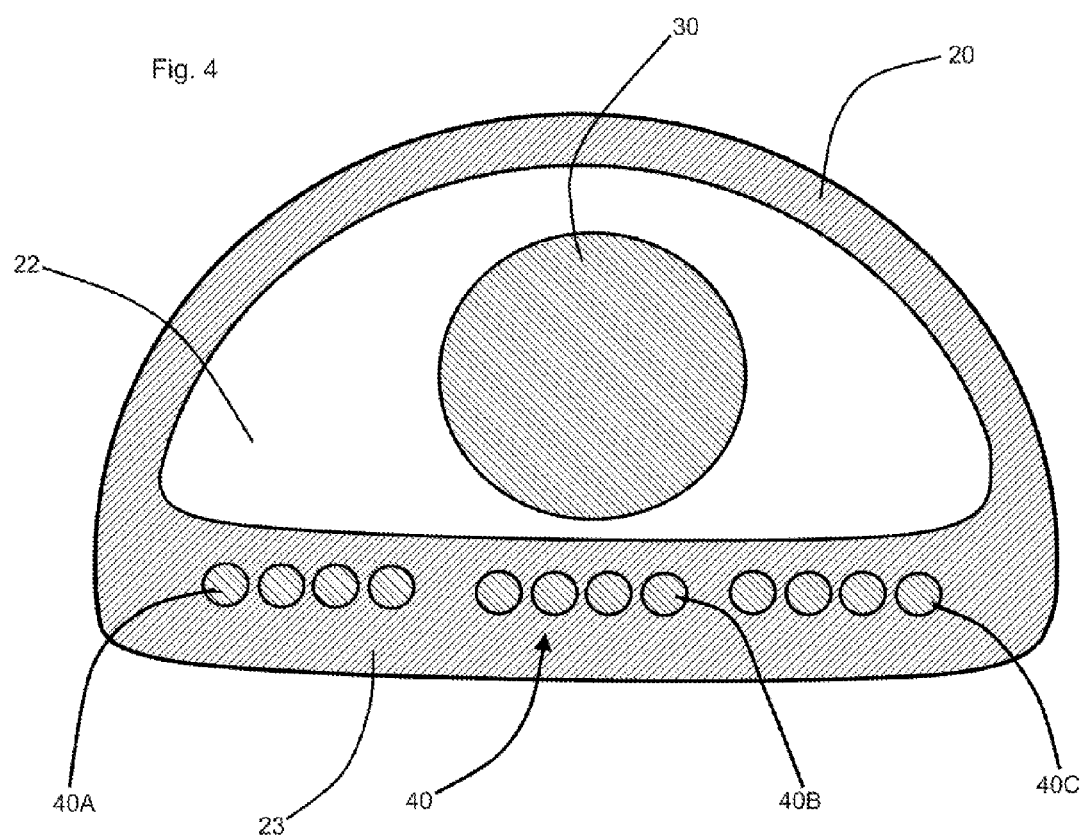

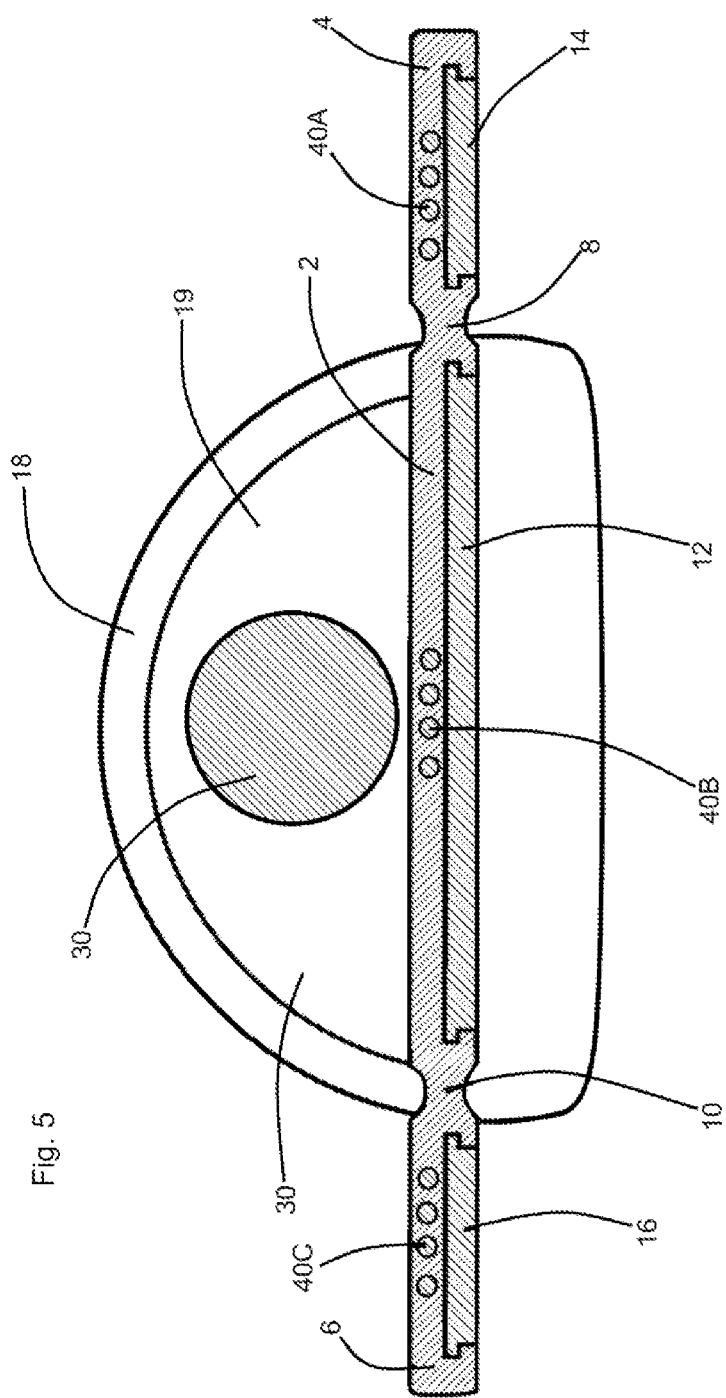

ASSEMBLY FOR PAIN SUPPRESSING ELECTRICAL STIMULATION OF A PATIENT'S NERVE

CLAIM OF BENEFIT OF FILING DATE OF PREVIOUSLY FILED U.S. PATENT APPLICATION

This patent application constitutes a divisional patent application claiming the benefit of the filing date of U.S. patent application Ser. No. 12/627,975, filed Nov. 30, 2009, and entitled "Assembly for Pain Suppressing Electrical Stimulation of a patient's Spinal Cord".

The inventor in the instant application is the same as the inventor in said application Ser. No. 12/627,095.

The specification of the instant application is identical to the specification in said application Ser. No. 12/627,095 with the exception that the title of the instant application has been changed to "Assembly for Pain Suppressing Electrical Stimulation of a Patient's Nerve". No new matter is introduced by virtue of such alteration of patent application title.

Claims 8-13 of said application Ser. No. 12/627,095 were withdrawn without prejudice from consideration in the prosecution of that application in response to the Examiner's division restriction. The claims of the instant divisional application (ie. Claims 1-6) are identical to the withdrawn Claims 8-13 of said application Ser. No. 12/627,095 with the exception that at every instance of appearance of the words "spinal cord", the word "nerve" is substituted in replacement. No new matter is inserted by virtue of such claims modification.

The drawings of the instant divisional application are identical to the drawings of said application Ser. No. 12/627,095.

The inventor's oath which was submitted upon the filing of said application Ser. No. 12/627,095 is incorporated herein by reference as the inventor's oath herein and said oath is contemporaneously refiled and resubmitted herewith.

This divisional application is filed prior to the abandonment or issuance as a U.S. patent of said application Ser. No. 12/627,095.

FIELD OF THE INVENTION

This invention relates to apparatus and assemblies for pain suppressing electrical stimulation of a patient's spinal cord. More particularly this invention relates to such apparatus which are adapted for percutaneous insertion into and extension along the pain patient's vertebral column.

BACKGROUND OF THE INVENTION

Assemblies which are adapted for electrical stimulation of a patient's spinal cord for pain suppression are known to be insertable percutaneously through a cannulas and into the patient's vertebral epidural space. During the performance of insertion procedures, such assemblies desirably exhibit a semi-rigid character within their elongated lead portions and within their electrical contact "paddle" head portions. Following epidural insertion and optimization of paddle head positioning, such assemblies desirably exhibit an alternative flexible and protrusion free character for enhancement of patient comfort during pain suppressing use. In order to minimize trauma to soft tissue structures during insertion procedures, such assemblies also desirably exhibit a small cross sectional size for insertion through a small diameter cannulas, and exhibit an enlarged electrical contact enhancing paddle head size after passage through such needle.

Known electrical stimulation pain suppression assemblies typically fail to exhibit one or more of the above described desirable characteristics.

The instant inventive assembly for pain suppressing electrical stimulation of a patient's spinal cord includes specialized structures which cause the assembly to exhibit and to function consistently with each of the above described desirable characteristics.

BRIEF SUMMARY OF THE INVENTION

The instant inventive apparatus and assembly for pain suppressing electrical stimulation of a patient's spinal cord is of the type which is extendable into the dorsal aspect of a patient's torso, epidurally and percutaneously. An extreme distal end of a paddle head component is preferably inserted via a hollow bored cannulas or needle, preferably a Tuhoy needle, to travel into and along a patient's vertebral epidural space. The assembly's paddle head component, along with its proximally extending flexible insulator lead slides over the dura which encases the patient's spinal cord, the assembly residing within the patient's vertebral epidural space. Upon positioning of the paddle head component of the assembly at a desired location within the patient's epidural space, the electrical stimulation lead may be advantageously operated by a physician to administer pulsating electrical shocks at a selected site over the spinal cord for suppression transmission of pain stimuli.

The insulator component of the instant inventive assembly preferably has a longitudinally elongated plastic body, is typically approximately 2½ feet in length, and preferably has a longitudinally extending hollow bore. The distal paddle head component of the assembly is preferably fixedly attached to or formed wholly with the extreme distal end of the hollow bored flexible insulator.

The paddle head component preferably carries and supports lateral, medial, and oppositely lateral series of electrical contact plates, and the lateral and oppositely lateral plates are preferably pivotally moveable via hinge connections with a medial panel. Contracting pivoting movement of such lateral and oppositely lateral components advantageously allows the paddle head of the assembly to assume a small cross sectional profile which facilitates passage of the paddle head through the bore of a small diameter Tuohy needle.

Upon distal emission of the paddle head from such Tuohy needle, such hinges allow, through a plastic memory function, the lateral and oppositely lateral components to outwardly extend to an electrical contact surface augmenting position.

In order to achieve a semi-rigid anti-buckling character within the flexible insulator and within the paddle head during insertion procedures, the insulator is preferably hollow bored and the distal end of the paddle head preferably presents a proximally opening stay end receiving traction socket.

Upon extension of a semi-rigid stay through the flexible insulator's hollow bore to engage such socket, the distal end of such stay may impose a pulling or traction force upon the paddle head which prevents undesirable buckling or back folding during insertion. After insertion, the semi-rigid stay may be withdrawn in order to enhance patient comfort.

A battery powered electric pulse generator of the type conventionally known in the art is preferably supplied, such generator being electrically connected to embedded wire leads which emerge at the extreme proximal end of the flexible insulator. Such pulse generator advantageously supplies pulsating electrical power to the embedded wire leads and to the paddle head's electrical contact plates. Electrical conduction of such electric pulses at a desired location over the patient's spinal cord are known in the neurological arts to effectively reduce and block chronic pain.

Accordingly, objects of the instant inventive assembly for pain suppressing electrical stimulation of a patient's spinal cord include the provision of a paddle head configuration which includes hingedly interconnected lateral, medial, and oppositely lateral components for compactness during cannulas needle insertion and for alternative augmentation of electrical contact surfaces following insertion and during use. The invention's objects further include the provision of a proximally opening stay end receiving traction socket for prevention of buckling of the paddle head during insertion.

Other and further objects, benefits, and advantages of the present invention will become known to those skilled in the art upon review of the Detailed Description which follows, and upon review of the appended drawings.

BRIEF DESCRIPTION OF THE DRAWINGS

FIG. 4 is a sectional view as indicated in FIG. 3.

FIG. 5 is an alternative sectional view as indicated in FIG. 3.

DETAILED DESCRIPTION OF A PREFERRED EMBODIMENT

Figure 1:
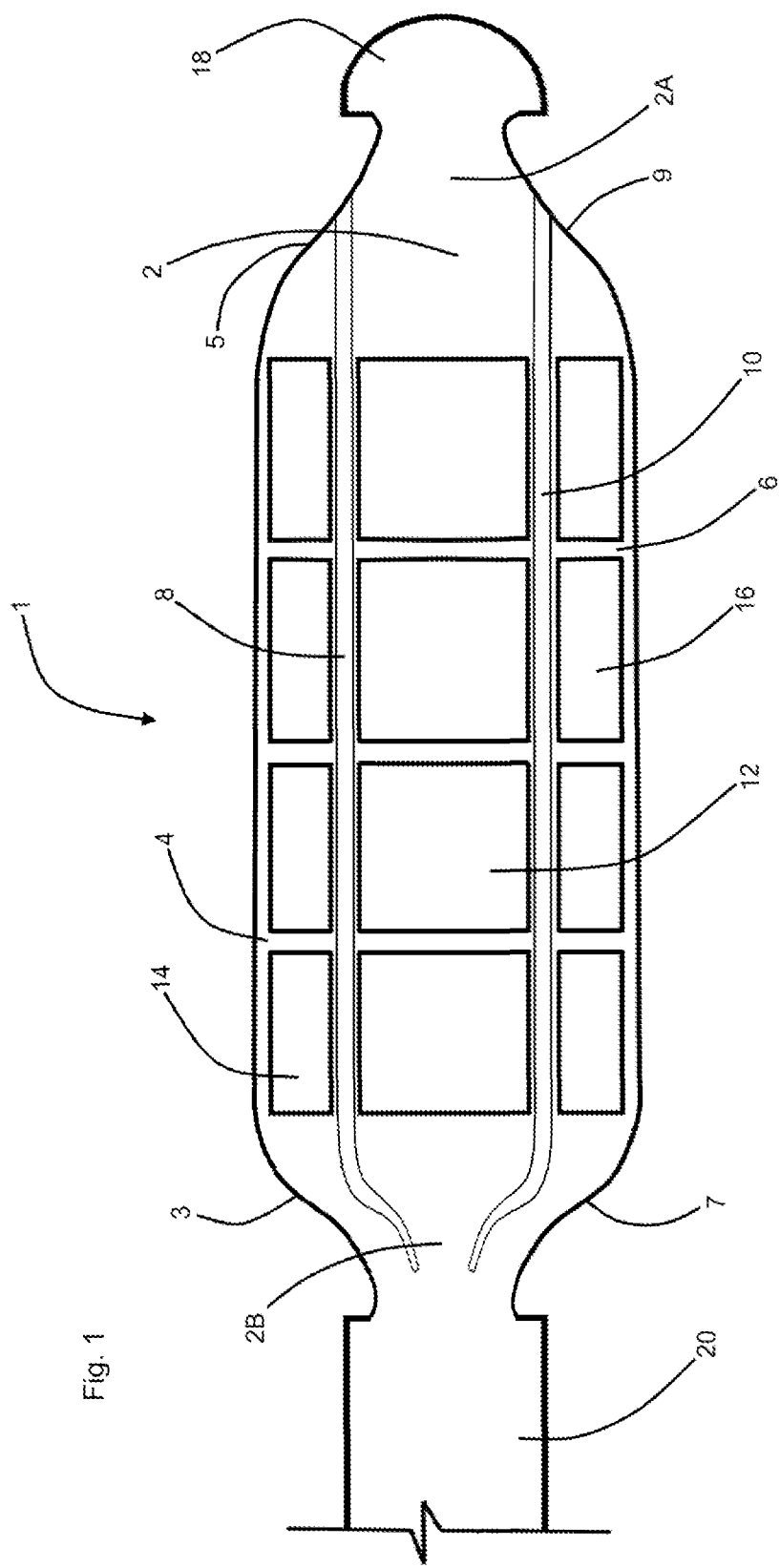
FIG. 1 is a plan view of an electrode side of the flexible paddle head component of the instant inventive assembly for pain suppressing electrical stimulation of a patient's spinal cord.
Figure 2:
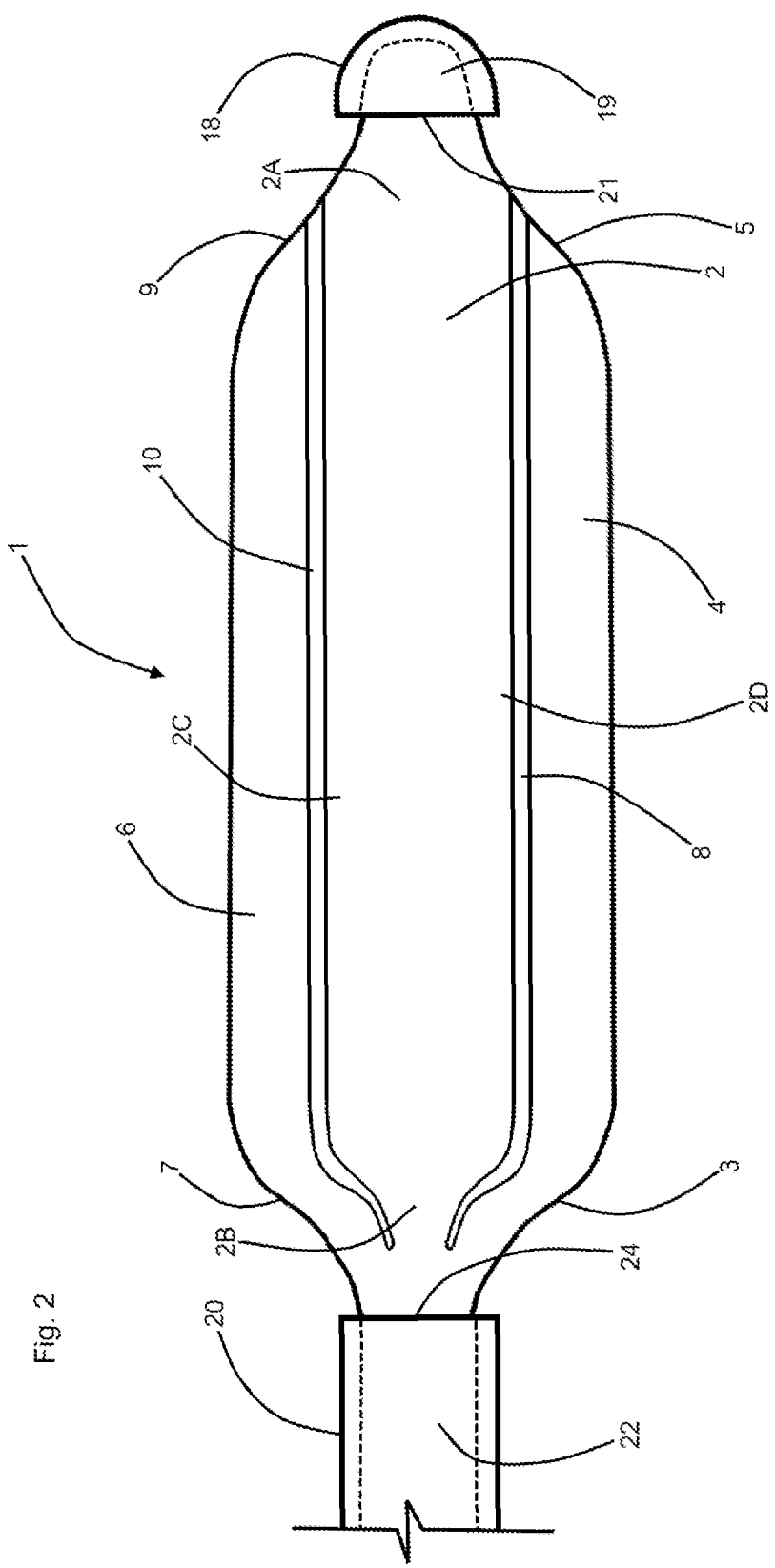
FIG. 2 is a reverse plan view of the structure depicted in FIG. 1.

Referring now to the drawings, and in particular to Drawing FIG. 1, a preferred embodiment of the distal aspects of the instant inventive assembly for pain suppressing electrical stimulation of a patient's spinal cord is referred to generally by Reference Arrow 1. Such assembly 1 preferably comprises at least a first or medial panel which is referred to generally by Reference Numeral 2. Referring further simultaneously to FIG. 2, the at least first panel 2 has a distal end 2A, a proximal end 2B, a lateral side 2C, and an oppositely lateral side 2D. The at least first panel 2 is preferably composed of durable and flexible injection molded plastic which enables the at least first panel 2 to serve functionally as a substrate structure which supports at least a first series or medial series of electrical contact plates 12.

The at least first or medial series of electrical contact plates 12 are preferably composed of a durable and corrosion resistant electrically conductive metal such as titanium or stainless steel, and such plates are preferably fixedly attached to the preferably plastic substrate medial panel 2 by means of a plastic injection over-molding process.

Figure 3:
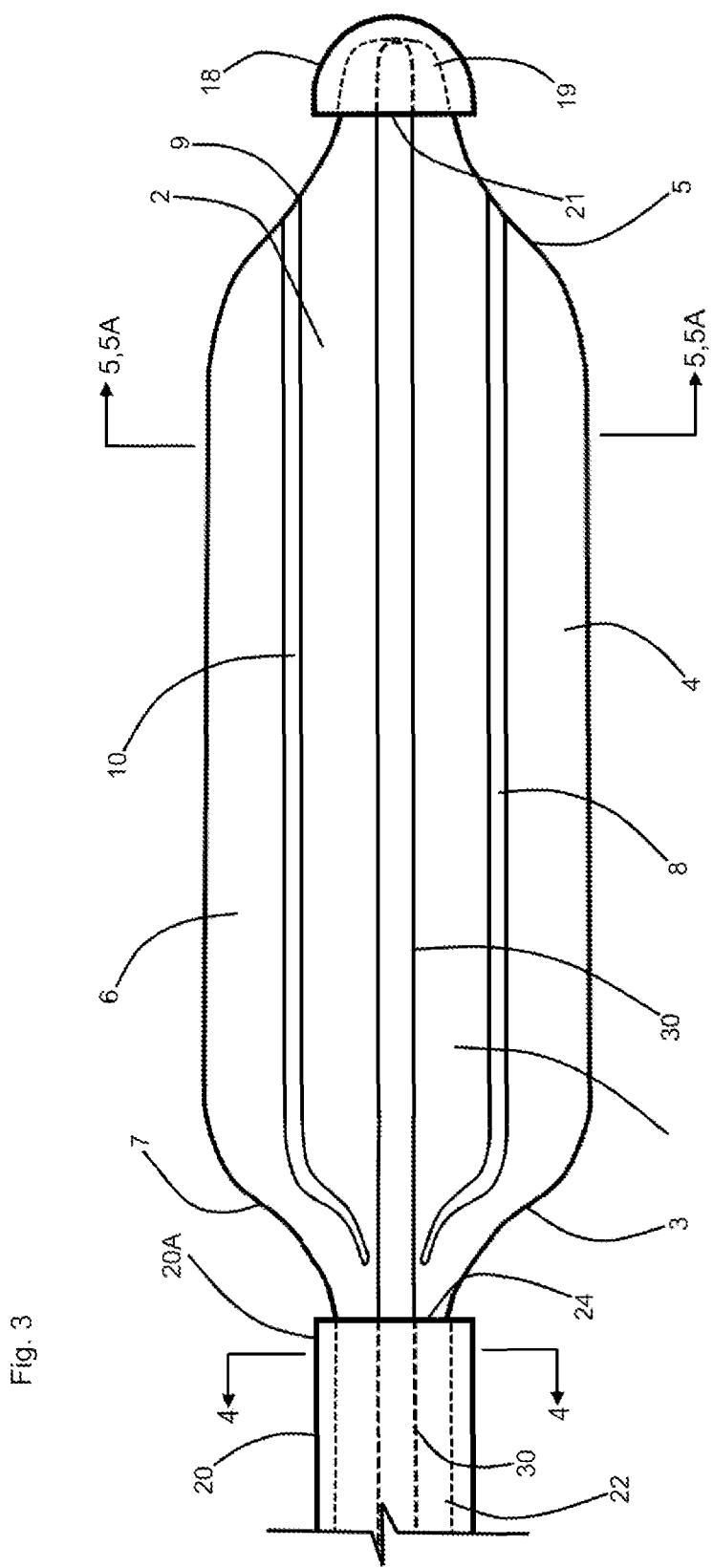
FIG. 3 redepicts the structure of FIG. 2, the view of FIG. 3 additionally including a temporarily installed semi-rigid stay component.

Referring simultaneously to FIGS. 1, 3, and 5, the at least first or medial series of electrical contact plates 12 preferably communicates electrically with a plurality of embedded electrically conductive wires 40B, such wires extending proximally along the longitudinal length of the panel 2. Referring further to FIGS. 2 and 4, an elongated a flexible insulator 20 which preferably has a small outside diameter between 1 millimeter and 1.2 millimeter, and which is preferably between two and three feet in length, has a distal end 20A which is fixedly attached to or is formed wholly with the proximal end 2B of the at least first or medial panel 2. The plastic overmolded and embedded electrically conductive wires 40B preferably further extend proximally through the body portion 23 of the flexible insulator 20, such wires 40B forming a subgroup of wire cluster 40. Each of the wires among the wire cluster 40 preferably extends within the lower wall 23 of the flexible insulator 20 to become electrically exposed at such insulator's extreme proximal end (not depicted within view). At such proximal end exposure, the wires 40 are advantageously subject to electrical contact and electrical current control via an electrical pulse generated (not depicted within views). The flexible insulator 20 preferably is composed of the same flexible and durable plastic material as the at least first or medial panel 2.

Referring to FIG. 1, the instant inventive assembly for pain suppressing electrical stimulation of a patient's spinal cord preferably further comprises lateral and oppositely lateral panels 4 and 6 which are preferably molded integrally with and are composed of the same flexible and durable plastic material as the at least first or medial panel 2. Similarly with the medial panel's attachment to and support of the at least first or medial series of electrical contact plates 12, the lateral and oppositely lateral panels 4 and 6 have attached thereto and provide substrate support to lateral and oppositely lateral series of electrical contact plates 14 and 16. Referring further simultaneously to FIG. 5, the lateral and oppositely lateral panels 4 and 6 further support embedded electrically conductive wires 40A and 40C which respectively communicate electrically with the lateral and oppositely lateral series of electrical contract plates 14 and 16. Referring further simultaneously to FIG. 4, such electrically conductive wires 40A and 40C extend, similarly with the electrically conductive wires 40B, proximally through and along the body portion 23 of the flexible insulator 20 as a part of wire cluster 40. The proximal ends of the electrically conductive wires 40A and 40C preferably emerge at the extreme proximal end of the flexible electrical insulator 20 for electronic pulse generating control, as described above.

Figure 5A:
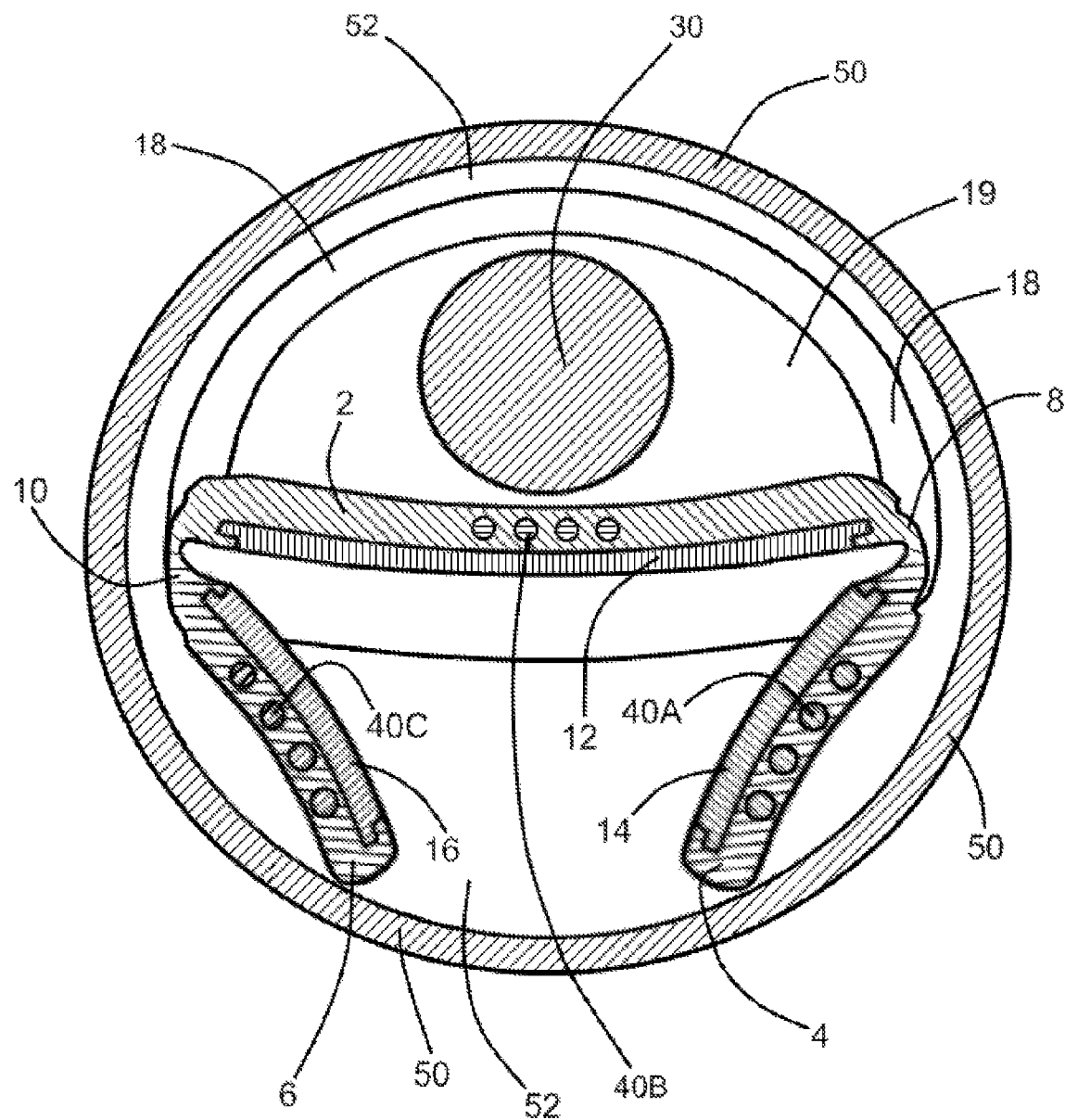
FIG. 5A redepicts FIG. 5, the view of FIG. 5A showing the paddle head component of the instant inventive assembly having lateral and oppositely lateral panels pivotally moved to their retracted compact positions, and further showing such panel nestingly received within the bore of a Tuohy needle.

Referring simultaneously to FIGS. 1, 3, 5, and 5A, hinge means are preferably provided for respectively pivotally connecting the lateral and oppositely lateral panels 4 and 6 to the lateral and oppositely lateral sides 2D and 2C of the at least first or medial panel 2. The hinge means is preferably adapted for facilitating pivotal movements of the lateral and oppositely lateral panels 4 and 6 between compact retracted positions as depicted in FIG. 5A and extended electrical contact surface augmenting positions as depicted in FIG. 5. In the depicted preferred embodiment, the hinge means comprises lateral and oppositely lateral living hinges 8 and 10, such hinges having an outwardly extending plastic memory character. Suitably, other commonly known hinge structures may be substituted for the preferred living hinges 8 and 10.

Upon pivotal movement of the lateral and oppositely lateral panels 4 and 6 to their retracted positions, it may be seen in FIG. 5A that each of the medial 2, lateral 4, and oppositely lateral 6 panels may compactly reside within the small (typically 1.4 mm) interior bore 52 of a Tuohy needle or cannulas 50. Upon distally directed emission of the paddle head 1 from the distal or pointed end of such Tuohy needle 50, the elastic plastic memory character of the preferred lateral and oppositely lateral living hinges 8 and 10 may advantageously laterally and oppositely laterally pivot and extend the lateral and oppositely lateral panels 4 and 6 to the electrical contact augmenting positions which are depicted in FIG. 5.

Referring in particular to FIGS. 1, 2, 3, and 5A, the leading or distal edges of the lateral and oppositely lateral panels 4 and 6 are preferably configured to present chamfered or beveled edges 5 and 9. Such edges 5 and 9 desirably prevent any catching or snagging of the paddle head 1 against an insertion or inlet edge of the Tohoy needle 50. In order to facilitate a reverse or proximally directed extraction of the paddle head 1 through such needle 50 without any such snagging or catching, the proximal edges of the lateral and oppositely lateral panels 4 and 6 preferably similarly present chamfered or beveled edges 3 and 7.

Referring simultaneously to FIGS. 1 and 5A, in use of the instant inventive assembly for pain suppressing electrical stimulation of a patient's spinal cord, the Tuohy needle or cannulas 50 may be initially inserted by a physician percutaneously over the dorsal aspect of a chronic pain patient's spine to extend between an adjacent pair of the patient's vertebrae. Inward extension of the cannulas 50 preferably ceases when the distal end of the cannulas emerges within the epidural space of the pain patient's spinal cord. Upon such insertion of the Tuohy needle 50, an open conduit between the epidural space and the outside environment is established. Thereafter, the extreme distal end of the inventive assembly may be inserted into the proximal end of and may be threaded through the Tuohy needle 50 until the paddle head 1 emerges within the patient's epidural space. Typically at the commencement of the insertion procedure, the physician so inserting the instant inventive assembly has inexact knowledge of the optimal location of the paddle head 1 over the patient's spinal cord for maximum suppression of transmission of pain stimuli. Such positioning knowledge is typically acquired only through the physician's execution of a series of trial and error positioning and repositioning steps accompanied by repeated electrical stimulating testing steps. Such insertion procedures may include repeated and various extensions of and withdrawals of the paddle head 1 along the epidural space. During such necessary repositioning and testing of the function of the paddle head 1, the instant inventive assembly desirably functions in the manner of a probe, and in order to effectively function as a probe, the assembly desirably temporarily exhibits a semi-rigid character. The desirable temporary semi-rigid character prevents the insulator and paddle head from buckling upon frictional contact with tissues lining the patient's epidural space. In order to temporarily facilitate such desirable semi-rigid probe function, referring to FIG. 4, the flexible insulator 20 preferably forms and defines a longitudinally extending hollow bore 22 which slidably receives a semi-rigid stay 30.

Referring simultaneously to FIGS. 1, 2, and 3, a proximally opening stay end receiving traction socket 18 is preferably fixedly attached to or formed wholly with the extreme distal end 2A of the medial or at least first panel 2, such socket 18 having a proximal opening 21 and forming a concavity 19. Upon full distal extension of the semi-rigid stay 30 through the hollow bore 22 of the flexible insulator 20, the extreme distal end of such stay 30 may enter and become captured within the concavity 19 of the proximally opening traction socket 18. Upon such stay end capture, the stay 30 may advantageously exert pulling traction force upon the distal end of the paddle head 1. Upon probing extensions of the paddle head 1 through the patient's epidural space, and upon frictional contact of the paddle head with tissues therein, such traction effect advantageously prevents any undesirable buckling or proximal overfolding of the paddle head 1.

In order to prevent electrical interference of the stay 30 with the function of the contact plates 12, 14, and 16 during the insertion and positioning process, the bore opening 24 and the socket opening 21 preferably overlie the non-electrode side of the paddle head 1, such arrangement preventing the stay 30 from electrically shielding the contact plates.

Referring simultaneously to FIGS. 2 and 5A, the hollow bore 22 of the flexible insulator 20 and the concavity 19 of the traction socket 18 may suitably, though less desirably, be alternatively configured continuously with each other to form a continuous stay guiding conduit which longitudinally traverses the non-electrode side of the paddle head 1. However, such continuous conduit configuration undesirably takes up needed space within the bore of the Tuhoy needle 50 for compact paddle head containment. Such configuration also undesirably lends uncomfortable rigidity to the paddle head 1 and creates an uncomfortable paddle head protrusion. In order to ameliorate such undesirable paddle head characteristics, the hollow bore 22 of the flexible insulator 20 preferably presents a distal opening 24 at the proximal end 2B of medial or at least first panel 2. In such preferred configuration, upon full distal extension of the semi-rigid stay 30 as depicted in FIG. 3, the distal end of such stay 30 may temporarily bridge longitudinally across the non-electrode side of the paddle head 2. Where such temporary paddle head bridging configuration is included within the assembly, the paddle head 1 may advantageously function as a semi-rigid probe during insertion and location testing repositionings, and may alternatively serve as a flexible and comfortable insulator lead and paddle head upon location at an optimal position over the patient's spinal cord.

While the principles of the invention have been made clear in the above illustrative embodiment, those skilled in the art may make modifications in the structure, arrangement, portions and components of the invention without departing from those principles. Accordingly, it is intended that the description and drawings be interpreted as illustrative and not in the limiting sense, and that the invention be given a scope commensurate with the appended claims.

I claim:

1. An assembly for pain suppressing electrical stimulation of a patient's nerve, the assembly comprising:
   (a) at least a first series of electrical contact plates;
   (b) at least a first panel having proximal and distal ends and having lateral and oppositely lateral sides, the at least first series of electrical contact plates being fixedly attached to the at least first panel;
   (c) a plurality of proximally extending electrically conductive wires, each wire among said plurality of wires having a distal end, each of said distal ends communicating electrically with one of the plates among the at least first series of electrical contact plates;
   (d) a flexible insulator fixedly attached to or formed wholly with the at least first panel's proximal end, the flexible insulator defining a longitudinally extending hollow bore;
   (e) a proximally opening traction socket fixedly attached to or formed wholly with the at least first panel's distal end; and
   (f) a semi-rigid stay having a distal end, the semi-rigid stay being receivable within the hollow bore, the semi-rigid stay, upon full distal extension through the hollow bore, being engageable with the proximally opening traction socket.

2. The assembly for pain suppressing electrical stimulation of a patient's nerve of claim 1 wherein the at least first panel has electrode and non-electrode sides, and wherein the longitudinally extending hollow bore has a distal opening positioned at the at least first panel's proximal end.

3. The assembly for pain suppressing electrical stimulation of a patient's nerve of claim 2 wherein the longitudinally extending hollow bore's distal opening is further positioned to overlie the at least first panel's non-electrode side.

4. The assembly for pain suppressing electrical stimulation of a patient's nerve of claim 3 wherein the proximally opening traction socket is positioned with respect to hollow bore's distal opening so that, upon the semi-rigid stay's engagement with the proximally opening traction socket, said stay's distal end bridges longitudinally over the at least first panel's non-electrode side.

5. The assembly for pain suppressing electrical stimulation of a patient's nerve of claim 4 further comprising lateral and oppositely lateral series of electrical contact plates, lateral and oppositely lateral panels, and hinge means, the lateral and oppositely lateral series of electrical contact plates being respectively fixedly attached to the lateral and oppositely lateral panels, and the hinge means respectively pivotally attaching the lateral and oppositely lateral panels to the at least first panel's lateral and oppositely lateral sides, the hinge means facilitating movements of the lateral and oppositely lateral panels between compact retracted positions and electrical contact surface augmenting extended positions.

6. The assembly for pain suppressing electrical stimulation of a patient's nerve of claim 5 further comprising lateral and oppositely lateral pluralities of proximally extending electrically conductive wires, each wire among said pluralities of wires having a distal end, and each of said distal ends communicating electrically with one of the plates among the lateral and oppositely lateral series of electrical contact plates.

* * * * *